(12) United States Patent
Gruber et al.

(10) Patent No.: US 10,034,830 B2
(45) Date of Patent: Jul. 31, 2018

(54) COMPOSITION FOR TREATING SKIN PIGMENTATION

(71) Applicant: LONZA WALKERSVILLE, INC., Walkersville, MD (US)

(72) Inventors: James V. Gruber, Washington, NJ (US); Philip L. Ludwig, Dunellen, NJ (US)

(73) Assignee: LONZA LTD., Visp (CH)

( * ) Notice: Subject to any disclaimer, the term of this patent is extended or adjusted under 35 U.S.C. 154(b) by 365 days.

(21) Appl. No.: 14/660,043

(22) Filed: Mar. 17, 2015

(65) Prior Publication Data

US 2015/0190337 A1    Jul. 9, 2015

Related U.S. Application Data

(62) Division of application No. 13/720,402, filed on Dec. 19, 2012, now abandoned.

(60) Provisional application No. 61/579,178, filed on Dec. 22, 2011.

(51) Int. Cl.
| | |
|---|---|
| *A61K 8/97* | (2017.01) |
| *A61Q 19/02* | (2006.01) |
| *C12Q 1/25* | (2006.01) |
| *G01N 33/72* | (2006.01) |
| *G01N 33/50* | (2006.01) |

(52) U.S. Cl.
CPC .............. *A61K 8/97* (2013.01); *A61Q 19/02* (2013.01); *C12Q 1/25* (2013.01); *G01N 33/50* (2013.01); *G01N 33/728* (2013.01); *A61K 2800/40* (2013.01); *G01N 2500/04* (2013.01); *G01N 2500/20* (2013.01); *Y10T 436/145555* (2015.01); *Y10T 436/146666* (2015.01)

(58) Field of Classification Search
None
See application file for complete search history.

(56) References Cited

U.S. PATENT DOCUMENTS

| | | | |
|---|---|---|---|
| 3,067,103 A * | 12/1962 | Chen ................ | A61K 9/0014 424/776 |
| 6,607,735 B2 | 8/2003 | Cole et al. | |
| 7,288,263 B2 | 10/2007 | Boxrud | |
| 2007/0122492 A1* | 5/2007 | Behr et al. ............ | 424/725 |
| 2009/0028826 A1 | 1/2009 | Breton et al. | |
| 2009/0263435 A1 | 10/2009 | Potin et al. | |
| 2010/0247563 A1* | 9/2010 | Hines et al. ......... | 424/195.16 |
| 2011/0250227 A1* | 10/2011 | Elraz ................ | A61K 36/185 424/195.17 |
| 2012/0045405 A1* | 2/2012 | Gilman ............... | A61K 8/31 424/62 |

OTHER PUBLICATIONS

Pirone C, The animal pigment bilirubin identified in *Strelitzia reginae*, the bird of paradise flower, HortScience, 45(9), 1411-1415, 2010.*

Pirone C., The animal pigment bilirubin identified in *Stretlizia regina*, the bird of paradise flower, HortSci., 2010, 45 (9), 1411-1415.

* cited by examiner

*Primary Examiner* — Celeste A Roney
(74) *Attorney, Agent, or Firm* — McBee Moore Woodward & Vanik IP, LLC

(57) ABSTRACT

The invention relates to a topical composition containing a bilirubin-producing plant extract. In particular, the bilirubin-producing plant extract is obtained from the genus *Stelitzia*. When topically applied to skin, the composition is effective in accelerating the degradation of heme by-products such as bilirubin present in the skin.

20 Claims, 1 Drawing Sheet

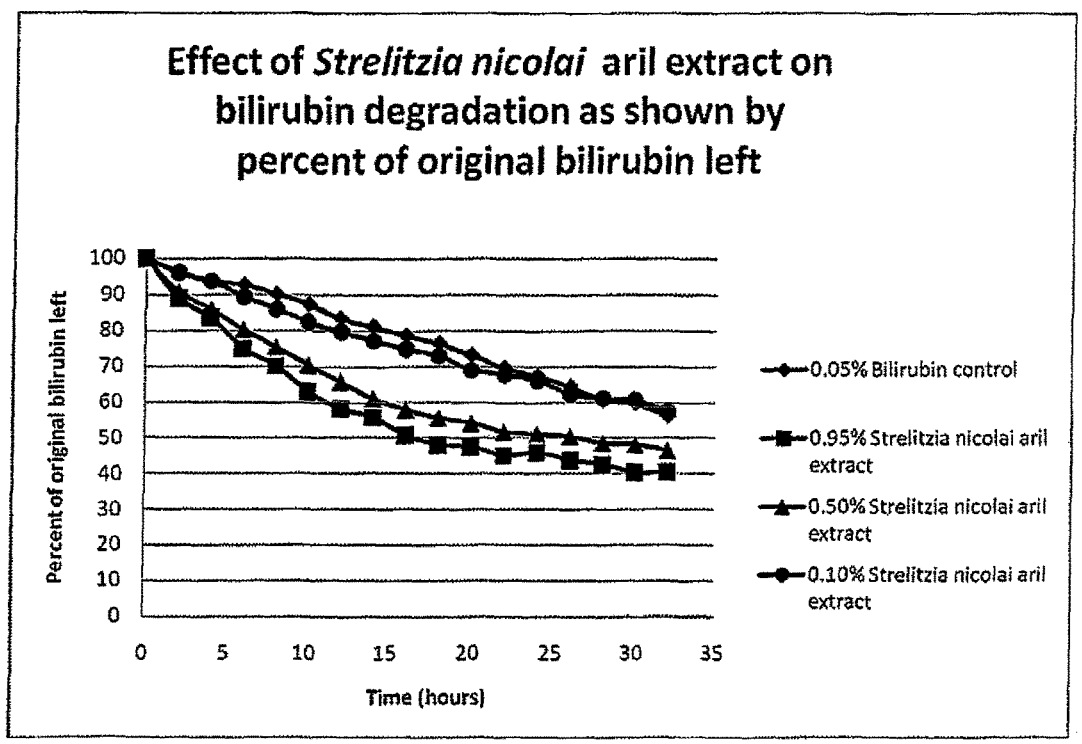

COMPOSITION FOR TREATING SKIN PIGMENTATION

CROSS-REFERENCE TO RELATED APPLICATIONS

This application is a divisional application of U.S. application Ser. No. 13/720,402, filed Dec. 19, 2012, which claims priority to U.S. Application No. 61/579,178 filed Dec. 22, 2011, which are herein incorporated by reference in their entirety.

FIELD OF THE INVENTION

The present invention relates to compositions effective in accelerating the degradation of heme by-product accumulation in the skin, particularly bilirubin accumulated in bruised skin or areas under the eyes. More particularly, the present invention relates to topical compositions containing an extract derived from the plants of the genus *Strelitzia* or *Phenakospermum*, and to the manufacture and methods of using such compositions.

BACKGROUND OF INVENTION

The human body comprises a number of pigmented molecules that contain porphyrin-containing components that comprise iron as part of the porphyrin molecule. These are frequently referred to as "heme" type molecules. Hemoglobin, and to a lesser extent, myoglobin, neuroglobin and cytoglobin are well-known porphyrin-containing molecules. Hemoglobin in particular is important for the skin because it is one of the primary pigments that define skin tone and color. The fine vascularization of the skin is also important for the "rosy" glow attributed to healthy skin.

When heme-containing molecules like hemoglobin break down in the body, they can convert to a number of degradation products that are also pigmented. For example, hemoglobin first converts to biliverdin and then to bilirubin, which is eventually removed from the body through the liver and kidneys. As heme degradation by-products accumulate, the body may also create certain proteins like ferritin and hemosiderin that will trap free iron and store it to keep it from reaching toxic levels in the skin. Most of these degradation by-products are also highly colored with dark blues, browns, and yellows being common colors for them. When these molecules accumulate near the surface of the skin, they can manifest themselves as undesirable spots such as bruises, dark circles, and other skin pigment disorders.

Around the eyes, the accumulation of heme degradation by-products can cause what is commonly referred to as dark circles. It is believed that the dark circles on the skin that surrounds the eyes are the result of a number of factors that are related to impaired vascular circulation around the eyes. This includes principally blood vessel leakage, accumulation of blood and blood degradation by-products around the eyes, and ineffective drainage of the blood and blood by-products through the lymph system surrounding the eyes. These conditions can be exacerbated at night when blood flow slows and the resting head is not significantly raised above the heart as it is during the day.

During sleep, blood and blood degradation by-products gather in the rich vascular beds under the eyes. These conditions can be exacerbated by fatigue, stress, drug and alcohol use, and other extraneous factors. Similar problems can occur in skin that is damaged by bruising usually from some form of blunt force trauma which causes the blood vessels in the skin to leak but does not result in breakage of the skin to provide external bleeding relief. In these circumstances, the blood pools near the wound and the degradation by-products accumulate. Likewise, when the skin is bruised, the accumulation of blood and blood degradation byproducts give the bruise the appearance of a dark purple to pale yellow blemish depending on the age of the bruise.

Most topical products designed to treat conditions such as dark circles and bruising are pigments intended to mask the discoloration. While these products can be helpful, they have to be carefully blended with the surrounding skin color, which changes throughout the day, and so are only a partial solution to the problem. Some products in the market are suggested to improve under eye color problems. In particular, it is well-established that the use of products that contain yeast extracts, such as for example, Preparation-H®, a product intended to treat hemorrhoids, is used regularly to also treat dark circles under the eyes. It is believed that the yeast extracts help to reduce inflammation, which is also associated with vasodilation and increased blood accumulation. Another popular under eye remedy is the use of sliced cucumbers. Slices of cucumbers placed on the eye are suggested to reduce swelling and inflammation as well as possibly reducing melanin accumulation around the eye, which is another source of non-heme pigment that can contribute to darkened skin around the eyes.

Heretofore, methods that are said to reduce the size of the blood vessels under the eyes and thereby reduce blood flow around the eyes are known. For example, U.S. Pat. No. 7,288,263 discloses a method intended to reduce vascularization around the eyes using pheniramine salts as vasoconstrictors. Likewise, U.S. Pat. No. 6,607,735 discloses a method intended to diminish pooling of blood around the eyes by employing chemicals called alkanolamines. Understandingly, the use of harsh chemicals for treatments around the eyes is not welcomed by many consumers as the eye is sensitive to stinging and irritating chemicals. Accordingly, other patents disclose less harsh methods to control under eye color. For example, U.S. Pub. No. 2009/0263435 discloses extracts containing natural xanthines, such as caffeine, to help minimize dark circles. Similarly, U.S. Pub. No. 2009/0028826 discloses the use of bacterial extracts from thermal waters that is alleged to help improve dark circles under the eyes.

What all of these prior inventions fail to disclose are methods to actually accelerate the degradation of the heme by-products as a means to control under eye color.

Accordingly, there is a need in the art for a solution to bilirubin accumulation in the skin that is natural and plant-based. The present invention provides a solution.

SUMMARY OF THE INVENTION

In one aspect, the present invention comprises a topical composition for accelerating the degradation of bilirubin accumulated in the skin. The composition includes (a) an extract derived from the plants of the genus *Strelitzia* or *Phenakospermum*, (b) a preservative present at an amount sufficient to provide sterilizing or biostatic efficacy with respect to component (a); and (c) a dermatologically-acceptable vehicle. In one embodiment, component (a) is present in an amount from about 0.05% to about 20%, preferably from about 0.1% to about 10%, more preferable from about 0.1% to about 5.0%, component (b) is from about 0.001% to about 3.0%, preferably from about 0.01% to about 2.0%, more preferable from about 0.1% to about 1.0%. Component (c) is from about 75% to about 99.05%, preferably from about 80% to about 95%, more preferably from about 85% to about 90%.

In another aspect, the present invention comprises a composition concentrate containing (a) an extract derived from the plants of the genus *Strelitzia* or *Phenakospermum*, (b) a preservative present at an amount sufficient to provide sterilizing or biostatic efficacy with respect to component (a), wherein the Non-Volatile Matter (NVM) of component (a) is present in an amount of about 0.001% to about 20% by weight of the composition concentrate, with 0.01% to 15% being preferred, and 0.1% to 15.0% being more preferred, and component (b) is present in an amount of about 0.001% to about 3% by weight of the composition concentrate, with 0.01% to about 2.0% being more preferred and 0.1% to about 1.0% being most preferred.

In yet another aspect, the present invention comprises a process for preparing the topical composition of the invention. The process includes contacting a plant extract derived from the plants of the genus *Strelitzia* or *Phenakospermum* with a preservative and a dermatologically-acceptable vehicle thereby making the topical composition.

In yet another aspect, the present invention comprises a method for accelerating the degradation of bilirubin accumulated in the skin. The method includes contacting the skin with the topical composition of the invention.

These and other aspects will become apparent upon reading the detailed description of the invention.

BRIEF DESCRIPTION OF THE DRAWINGS

The present invention is further illustrated by the following non-limiting drawings and examples.

FIG. 1 illustrates the effect of *Strelitzia nicolai* aril extract on bilirubin degradation.

DESCRIPTION OF INVENTION

It has now been surprisingly found that the extracts of arils from plants of the genus *Strelitzia* and *Phenakospermum* contain components which accelerate bilirubin degradation. It has further been surprisingly found that these components, when topically applied to the skin accelerate the degradation of heme by-products such as bilirubin accumulated in the skin, particularly in skin that is bruised or in areas under the eyes.

The extracts of the invention can be derived from any bilirubin-producing plant. In one embodiment, the extracts are derived from plants of the genus *Strelitzia* or *Phenakospermum*, preferably genus *Strelitzia*, most preferably from the plant *Strelitzia nicolai*, which is more commonly referred to as the White Bird of Paradise. The extracts can be derived from the whole plant, part of the plant, the seed of the plant, or cell culture of the plant. Preferably, the extracts are derived from the seeds of the plant, more preferably the arils of the seeds of the plant. In one embodiment, the extracts are taken from the arils of the seeds of the plant *Strelitzia nicolai*.

Extracts of the present invention can be made by methods well known to those skilled in the art. For example, the arils of the plant seeds from plants of the genus *Strelitzia* and *Phenakospermum* such as *Strelitzia nicolai* can be removed from the seeds and extracted using a variety of extraction techniques not limited to solvent, steam, liquid $CO_2$ and the like. A preferred method is includes solvent extraction using non-organic solvents such as, for example, water. The water may be buffered or modified by the addition of salts or surfactants to enhance the extraction process, but water is the essential solvent for extraction of the arils. The composition of the extract is complex, potentially containing any number of ingredients known to exist in the plant, plant seeds or plant arils. These may include biological components such as amino acid containing ingredients such as, for example, proteins, enzymes, cytokines and glycoproteins, or sugar-containing moieties such as, for example, oligosaccharides, polysaccharides, disaccharides, and the like. Additionally, the extract may contain simple organic molecules such as, for example, isoprene-containing moieties, flavonoids and isoflavonoids, plant-derived acids and plant-derived bases and the like.

Purification of individual actives from the plant extract can be accomplished using known purification methods such as chromatography, distillation, filtration and the like. However, removal or concentration of actives from the plant extract is not a requirement for the efficacy of the plant extract to accelerate bilirubin degradation.

The process of bilirubin degradation demonstrated by extracts of the arils of plants of the genus *Strelitzia* and *Phenakospermum* can be measured by a method comprising the following steps: (a) dispersing or dissolving bilirubin in water; (b) adding measured amounts of the extract of the bilirubin-producing plant; and (c) measuring bilirubin degradation verses time using an analytical method sensitive to detecting bilirubin and its degradation by-products. The bilirubin degradation can be measured using either UV, IR, HPLC or other sensitive measuring analytical techniques. The preferred method is by chromatography of bilirubin in aqueous solution using UV-spectrophotometric detection to analyze the degradation of bilirubin and the accumulation of bilirubin byproducts.

Dry basis solids content is measured by removing all volatile components from the extract using a thermal oven until the dried residues no longer change in weight. This is often referred to as Non-Volatile Matter (NVM). The composition of the aril extract can comprise a dry basis solids (NVM) content of 0.001-20%, preferably 0.01-15%, most preferably 0.1-15.0%

Advantageously, a preservative is added to the extract of the present invention to protect the extract against contamination by undesirable airborne microorganisms. As used herein, a preservative is defined as an ingredient that renders the extract sterile or biostatic to undesirable microorganisms. Preservatives are well known to those skilled in the art and can include for example, alcohols, glycols, parabens, hydantoins, quaternary-nitrogen containing compounds, isothiazolinones, aldehyde-releasing compounds and halogenated compounds, and combinations thereof. A particularly effective preservative is phenoxyethanol.

Accordingly, in one embodiment, the present invention provides a composition concentrate comprising: (a) an extract derived from a bilirubin producing plant; (b) a preservative present in an amount sufficient to provide sterilizing and biostatic effect on component (a), wherein component (a) is present in an amount of from about 0.001% to about 20% by dry (NVM) weight of the composition, and component (b) is present in an amount of from 0.001% to 3.0%, advantageously from about 0.01% to about 2.0%, more advantageously from about 0.1% to about 1.0% by weight of the total composition. In a preferred embodiment, the extract from the bilirubin-producing plant is selected from the genus *Strelitzia* or *Phenakospermum*.

The extracts of the present invention are intended for topical or therapeutic applications on the skin of mammals, in particular humans, where there is concern for darkening of the skin due to accumulation of blood and blood degradation by-products. In particular, conditions such as bruising (ecchymosis) or dark circles under the eyes (periorbitalhyperchromia), spider veins (telangiectasia) and port wine stains (naevusflammeus) are all conditions known to have excessive blood expression as a source for skin color changes.

The extracts of the present invention can be applied to the skin in forms well known to those skilled in the art including, but not limited to, direct application of the extract onto the skin or as a composition in a more user-friendly form such as a cream, lotion, gel, serum, soap, stick, powder or the like. The composition can be applied as a leave-on product or as a product intended to be rinsed off the skin immediately after applications such as, for example, bodywashes, shampoos and the like.

The efficacy of the product can be further enhanced by including the extract in delivery systems such as, for example, liposomes, niasomes, polymerisomes, dendrimerosomes and the like or through penetration enhancing mechanisms such as, for example, iontophoresis. Another effective form of delivery can be by way of patches or masks containing the extract that are left on the skin for an extended period of time. The extract may also be included in anhydrous systems by removal of the extraction solvent by any method known to those skilled in the art such as, for example, freeze drying, spray drying, belt drying and the like. In the anhydrous form, the product can be included in anhydrous gels, such as, for example, silicone gels or in anhydrous powders such as, for example, foundations and pressed powders. The extract can be used alone or in combination with other ingredients such as, for example, rheology modifiers, emulsifiers, emollients, feel-modifiers, solvents, preservatives and other actives. The extract could also form part of a fermentation media in which the active is either blended or added directly to a fermentation using living cells such as, for example, prokaryotes, eukaryotes, molds, fungi and the like.

In one embodiment, the invention relates to a topical composition for controlling bilirubin degradation. The composition is further intended to be able to diminish dark pigments of the human skin when applied topically. The topical composition comprises (a) an extract from a bilirubin-producing plant; (b) a preservative; and (c) a dermatologically-acceptable vehicle.

The extract of the present invention can be used in a topical composition in a range from about 0.05-20.0%, more preferably in a range from about 0.1-10%, most preferably in a range from about 0.1-5.0% in the final composition intended for application on the skin. In the topical composition, the preservative is present in an amount from about 0.001% to about 3.0%, preferably from about 0.01% to about 2.0%, more preferably, from about 0.1% to about 1.0%.

The phrase "dermatologically-acceptable carrier", as used herein, means that the carrier is suitable for topical application to the skin, has good aesthetic properties, is compatible with the actives of the present invention and any other components, and will not cause any safety or toxicity concerns.

The carrier can be a wide variety of forms. For example, emulsion carriers, including, but not limited to, oil-in-water, water-in-oil, water-in-oil-in-water, oil-in-water-in-oil, and oil-in-water-in-silicone emulsions, are useful herein. These emulsions cover a broad range of viscosities, e.g., from about 100 cps to about 200,000 cps. These emulsions can be delivered in the form of sprays using either mechanical pump containers or pressurized aerosol containers using conventional propellants. These carriers can also be delivered in the form of a hair mousse. Other suitable topical carriers include anhydrous liquid solvents such as oils, alcohols, and silicones (e.g., mineral oil, ethanol, isopropanol, dimethicone, cyclomethicone, and the like); aqueous-based single phase liquid solvents (e.g., hydro-alcoholic solvent systems); and thickened versions of these anhydrous and aqueous-based single phase solvents (e.g., where the viscosity of the solvent has been increased to form a solid or semi-solid by the addition of appropriate gums, resins, waxes, polymers, salts, and the like). Examples of topical carrier systems useful in the present invention are described in the following references, each of which are herein incorporated by reference in their entirety: "Sun Products Formulary" Cosmetics & Toiletries, vol. 105, pp. 122-139 (December 1990); "Sun Products Formulary", Cosmetics & Toiletries, vol. 102, pp. 117-136 (March 1987); U.S. Pat. No. 4,960,764 to Figueroa et al., issued Oct. 2, 1990; and U.S. Pat. No. 4,254,105 to Fukuda et al., issued Mar. 3, 1981.

The carriers can comprise from about 75% to about 99.05% by weight of the compositions of the present invention, preferably from about 80% to about 95%, and most preferably from about 85% to about 90%.

Preferred cosmetically and/or pharmaceutically acceptable topical carriers include hydro-alcoholic systems and oil-in-water emulsions. When the carrier is a hydro-alcoholic system, the carrier can comprise from about 0% to about 99% of ethanol, isopropanol, or mixtures thereof, and from about 1% to about 99% of water. More preferred is a carrier comprising from about 5% to about 60% of ethanol, isopropanol, or mixtures thereof, and from about 40% to about 95% of water. Especially preferred is a carrier comprising from about 20% to about 50% of ethanol, isopropanol, or mixtures thereof, and from about 50% to about 80% of water. When the carrier is an oil-in-water emulsion, the carrier can include any of the common excipient ingredients for preparing these emulsions. A more detailed discussion of suitable carriers is found in U.S. Pat. No. 5,605,894 to Blank et al., and, U.S. Pat. No. 5,681,852 to Bissett, both of which are herein incorporated by reference in their entirety.

The topical composition of the invention can optionally comprise additional functional ingredients such as, water, surfactants, emulsifiers, conditioners, emollients, waxes, oils, polymers, thickeners, fixatives, colorants, humectants, moisturizers, stabilizers, diluents, solvents and fragrances. In addition, the personal care composition may contain active ingredients such as botanicals, nutraceuticals, cosmeceuticals, therapeutics, pharmaceuticals, antifungals, antimicrobials, steroidal hormones, antidandruff agents, anti-acne components, sunscreens, preservatives and the like.

The topical composition of the invention can be made by contacting the extract from a bilirubin-producing plant, with a preservative and a dermatologically-acceptable vehicle.

In order to accelerate the degradation of bilirubin accumulated in the skin, the topical composition of the invention can be applied to the skin by any applicable method.

The following examples are intended to illustrate, but in no way limit the scope of the present invention. All parts and percentages are by weight based on the total weight of the composition and all temperatures are in degrees Celsius unless explicitly stated otherwise. All publications disclosed herein are incorporated by reference in their entireties.

EXAMPLE 1

Extraction of Arils of *Strelitzia nicolai* (Extract Concentrate)

A 1% aril solution was created by homogenizing 3 g of *Strelitzia nicolai* in 297 mL, pH 7.0 water in an ice bath using a Silverson L4R homogenizer (Chesham Bucks, England) at a speed of 4000 rpm for 10 minutes. The solution was further homogenized using a Niro Panda 2K (Bedford, N.H., U.S.A.) by passing the solution four times through the Niro homogenizer at 1000 bar pressure. After homogenization, the pH was brought up to 7.0 using a 0.1% NaOH solution.

The homogenized solution was filtered sequentially through four Whatman filters: #41, #2, #6, and #5, respectively, which correspond to 25 µm, 8 µm, 3 µm, and 2.5 µm. Finally, the solution was filtered through a 0.2 µm Nalgene filter. The solution was then concentrated to remove water in order to achieve a final NVM of *Strelitzia nicolai* aril extract concentrate having approximately 13% extract concentrate solids.

EXAMPLE 2

Bilirubin Degrading Ability of *Strelitzia nicolai* Aril Extract

For high pressure liquid chromatography (HPLC) analysis, a control of 0.050% bilirubin (Frontier Scientific, Logan, Utah) in pH 7.0 water was run along with samples of the *Strelitzia nicolai* aril extract concentrate of Example 1. The aril extract was diluted with pH 7.0 water to give a final concentration of 0.1%, 0.5% or 0.95% *Strelitzia nicolai* aril extract along with a 0.050% concentration of bilirubin in each solution.

HPLC solutions were prepared as described in Spivak and Yuey, Biochem. J. (1986) 234 (101-109), which is incorporated by reference herein. For HPLC solvent A, 0.04 M sodium acetate in methanol was prepared by dissolving 3.282 g sodium acetate from Sigma Chemical Co (St. Louis, Mo., USA) in 1000 mL methanol from Fisher Scientific (Pittsburgh, Pa., U.S.A.). For solvent B, 1% ammonium acetate in water was prepared by adding 10 ml of glacial acetic acid from Fisher Scientific to 990 ml of distilled water and titrating to pH 4.5 with concentrated $NH_3$ from Acros Organics (Geel, Belgium).

A Waters 2695 Alliance HPLC (Milford, Mass., U.S.A.) with a Waters 996 Photodiode array detector was used along with a Waters Nova-Pak C18 150×3.9 mm column with the Phenomenex security guard cartridge system KJO-4282. Solvent flow rate was 1.0 mL/min. Using solvents A and B, a linear gradient of 65% A: 35% B to 95% A in 7 min and 95% A to 75% A at minute 12 was prepared. Before separation, the HPLC column was equilibrated for 10 minutes. A 10 µl sample was injected into the column and allowed to elute for 10 minutes. The retention time for bilirubin was at 1.3-1.5 minutes analyzed at 450 nm wavelength.

The HPLC peak areas from the samples were analyzed. The percent of original bilirubin left in the sample was also determined.

Results of the analyses of various concentrations of diluted *Strelitzia nicolai* aril extract are shown in FIG. 1. As shown in FIG. 1, the zero time point for each chromatographic run was normalized to 100% regardless of the initial concentration so that the samples could be compared to one another and the rate of degradation could be determined from the slope of each line.

EXAMPLE 3

Preparation of *Strelitzia nicolai* Aril Extract in Oil-In-Water Emulsions

The *Strelitzia nicolai* aril extract from Example 1 was formulated into an oil-in-water emulsion using the following formulation and process:

| Ingredient | INCI Nomenclature | % |
|---|---|---|
| Phase (A) | | |
| Water | Water | Q.s to 100 |
| Versene ™ 100 | Tetrasodium EDTA | 0.10 |
| Glycerin | Glycerin | 2.00 |
| Carbopol ® Ultrez 10 | Carbomer | 0.20 |
| Phase (B) | | |
| Brookswax ™ D | Cetearyl Alcohol and Ceteareth-20 | 2.00 |
| Liquiwax DIADD** | DioctyldodecylDodecanedioate | 5.00 |
| Loronate TMP-TC | TrimethylolpropaneTricaprylate/Tricaprate | 2.00 |
| Arlacel ™ 60 | Sorbitan Stearate | 1.50 |
| Stearyl Alcohol | Stearyl alcohol | 0.20 |
| Cetyl Alcohol | Cetyl Alcohol | 0.50 |
| Stearic Acid | Stearic Acid | 0.50 |
| Myritol ® 318 | Caprylic/Capric Triglyceride | 2.00 |
| DC 200/100 cST | Dimethicone | 0.75 |
| Phase (C) | | |
| Water | Water | 5.00 |
| TEA 99 | Triethanolamine | 0.25 |
| Phase (D) | | |
| Extract Example 1 | — | 1.00 |
| Mikrokill ® COS | Phenoxyethanol, Caprylyl Glycol, and Chlorphenesin | 0.75 |

Procedure:
1. Combine Phase A and heat to 75° C. Mix until uniform.
2. Combine Phase B and heat to 75° C. Mix until uniform.
3. Add Phase B to Phase A while slow mixing Phase A. Mix for 20 minutes.
4. Add pre-mix Phase C to the batch and mix until uniform. Turn off the heat.
5. In a side kettle, pre-mix Phase D and add to the batch when it reaches a temperature below 40° C. Mix until uniform.
6. Add Mikrokie COS and fragrance of Phase E to the batch and mix until uniform.

EXAMPLE 4

Preparation of *Strelitzia nicolai* Aril Extract in Water-In-Oil Emulsions

The *Strelitzia nicolai* extract from Example 1 was formulated into a water-in-oil emulsion using the following formulation and process:

| Ingredient | INCI Nomenclature | % |
|---|---|---|
| Phase (A) | | |
| Water | Water | Q.s to 100 |
| Glycerin | Glycerin | 3.00 |
| Sodium Chloride | Sodium Chloride | 1.00 |
| Extract Example 1 | | 1.00 |
| Mikrokill ® COS | Phenoxyethanol, Caprylyl Glycol and Chlorphenesin | 0.75 |
| Phase (B) | | |
| SF1328 | Cyclomethicone and Dimethicone Copolyol | 10.00 |
| SF 1202 | Cyclomethicone | 8.50 |
| Gel Base Sil | Cyclomethicone and Dimethicone | 1.50 |
| Gel Base BSM-PE | Cyclomethicone, Dimethicone, PhenylTrimethicone, and Polyethylene | 1.50 |

Procedure:
1. Mix all of the ingredients of Phase A together.
2. Combine Phase B ingredients in order shown, thoroughly mixing each ingredient until homogeneous before adding the next ingredient.
3. Slowly add Phase A to Phase B with good mixing. Gradually increase agitation to high shear as mixture thickens. Continue agitation for 10 minutes.

EXAMPLE 5

Preparation of *Strelitzia nicolai* Aril Extract in Eye Gel Compositions

The *Strelitzia nicolai* aril extract from Example 1 was encapsulated into a liposomal composition. The encapsulated extract was then incorporated into an eye gel composition using the following process:

| Ingredient | INCI Nomenclature | % |
|---|---|---|
| Water | Water | Q.S to 100 |
| Carbopol ® Ultrez 21 Polymer | Acrylates/C10-30 Alkyl Acrylate Crosspolymer | 0.50 |
| Keltrol ® CG-SFT | Xanthan Gum | 0.10 |
| Butylene Glycol | Butylene Glycol | 5.00 |
| Mikrokill ® COS | Phenoxyethanol, Caprylyl Glycol and Chlorphenesin | 1.00 |
| Dow Corning ® 193 Surfactant | DimethiconeCopolyol | 0.30 |
| Disodium EDTA | Disodium EDTA | 0.10 |
| AMP 95 | Aminomethylpropanol | 0.45 |
| Liposome containing extract from Example 1 | | 1.00 |

Procedure:
1. Disperse the CarbopolUltrez 21 in water at 50° C. and add the Keltrol CG-SFT. Mix until uniform.
2. Add the Butylene Glycol, Mikrokill® COS, AMP 95, EDTA and Silicone 193. Mix until uniform.
3. Add the liposome containing the extract from example 1 with sweep agitation at 40° C. Mix until uniform.
4. Adjust pH to 5.5, if necessary.

EXAMPLE 6

Preparation of Encapsulated *Strelitzia nicolai* Aril Extract

The extract from Example 1 was encapsulated into a polymeric matrix using the techniques disclosed in Example 1 of U.S. Patent Application Publication No. 2003/0198682 A1, which is herein incorporated by reference in its entirety.

EXAMPLE 7

Preparation of *Strelitzia nicolai* Aril Extract Lipstick Compositions

The encapsulated *Strelitzia nicolai* aril extract in the polymeric matrix of Example 6 was formulated into a lipstick using the following formulation and process:

| Ingredient | INCI Nomenclature | % |
|---|---|---|
| Phase (A) | | |
| Castor Oil | *Ricinus Communis* (Castor) Seed Oil | 31.45 |
| Schercemol ™ TISC | Triisostearyl Citrate | 15.00 |
| Liquiwax ™ PolyIPL | Stearyl PPG-3 Myristyl Ether Dimer Dilinoleate | 5.00 |
| Liquiwax ™ PolyEFA | Octyldodecyl PPG-3 Myristyl Ether Dimer Dilinoloeate | 15.00 |
| Candelilla Wax | *Euphorbia Cerifer* (Candelilla) Wax | 6.00 |
| Ozokerite 170D | Ozokerite | 2.50 |
| Microwax SP 19 | Microcrystalline Wax | 3.50 |
| Carnauba Wax | *Copernicia cerifera* (carnauba) wax | 1.50 |
| Methylparaben | Methylparaben | 0.20 |
| Propylparaben | Propylparaben | 0.10 |
| Phase (B) | | |
| Color Grind | | |
| Soft-Tex ® Red 7 Ca Lake C19-7711 | Red 7 Lake | 0.04 |
| Soft-Tex ® Red 6 Ba Lake C19-7712 | Red 6 Lake | 0.17 |
| Red Iron Oxide A-1205 | Iron Oxides | 2.00 |
| Titanium Dioxide Ultra Fine 70110 | Titanium Dioxide | 2.00 |
| Black Iron Oxide C33-134 | Iron Oxides | 0.05 |
| Liquiwax ™ PolyEFA* | Octyldodecyl PPG-3 Myristyl Ether Dimer Dilinoloeate | 4.44 |
| Phase (C) | | |
| Ascorbyl Palmitate | Ascorbyl Palmitate | 0.05 |
| Flamenco ® Red Pearl | Mica and Titanium Dioxide | 10.00 |
| Powdered Extract from Example 6 | | 1.00 |

Procedure:
1. Combine Waxes, Oils and Preservatives (Phase A) and heat to 83-87° C.
2. Hold temperature and stir until homogeneous.
3. Drop temperature to 75-80° C., and add Phase B; mix until homogeneous.
4. Add the Flamenco® Red Pearl, Extract from example 1 and Ascorbyl palmitate (Phase C).
5. Pour into molds.

EXAMPLE 8

Preparation of *Strelitzia nicolai* Aril Extract Toner Compositions

The extract of Example 1 was formulated into an aqueous alcoholic tonic using the following formulation and process:

| Ingredient | INCI Nomenclature | % |
|---|---|---|
| Water | Water | Q.s To 100 |
| Betafin ® BP-20* | Betaine | 3.00 |
| Example 1 Extract | | 1.00 |
| Witch Hazel w/14% Alcohol | Water, Ethanol and Witch Hazel | 25.00 |
| Mikrokill ® COS | Phenoxyethanol, Caprylyl Glycol and Chlorphenesin | 0.75 |

Procedure:
1. Charge water and add Betafin® BP-20, and *Strelitzia nicolai* aril extract from example 1. Mix until uniform.
2. Add Witch Hazel and Mikrokill® COS. Mix until uniform.

EXAMPLE 9

Preparation of *Strelitzia nicolai* Aril Extract Body Wash Compositions

The *Strelitzia nicolai* aril extract of Example 1 was formulated into a body wash using the following formulation and process:

| Ingredient | INCI Nomenclature | % |
|---|---|---|
| Water | Water | Q.S to 100 |
| Hamp-ene ® Na2 | Disodium EDTA | 0.10 |
| Glycerin | Glycerin | 2.00 |
| Standapol ® WAQ-Special | Sodium Lauryl Sulfate | 30.00 |
| Standapol ® ES-2 | Sodium Laureth Sulfate | 25.00 |
| Cerasynt ® IP | Glycol Stearate, Stearic Acid and Aminomethyl Propanol | 0.50 |
| Velvetex ® BA-35 | CocoamidopropylBetaine | 7.00 |
| Cocamide MEA | Cocamide MEA | 2.00 |
| Mikrokill ® COS | Phenoxyethanol, Caprylyl Glycol and Chlorphenesin | 0.75 |
| Example 1 Extract | | 1.00 |

Procedure:
1. Heat Water to 70° C. and add Hamp-ene® Na2, Glycerin, and mix until uniform.
2. Keep temperature above 70° C. and add Standapol® WAQ-Special, Standapol® ES-2, Cerasynt® IP, Cocamide MEA, Velvetex® BA-35, and mix until uniform.
3. Cool to 45° C. and add Mikrokill® COS and Extract from example 1.
4. Mix until homogenous.

EXAMPLE 10

Preparation of *Strelitzia nicolai* Aril Extract in Yeast/*Strelitzia nicolai* Aril Extract Ferment Products The extract from Example 1 was included as part of a fermentation media containing the yeast *Saccharomyces cerevisiae*. A sample of the extract from Example 1 was placed into an aqueous mixture of Baker's Yeast growth media obtained from Red Star Yeast (Milwaukee, Wis.). The media was inoculated with an active *Saccharomyces cerevisiae* yeast culture also obtained from Red Star and the mixture was allowed to ferment under controlled aerobic conditions to provide a Live Yeast Cell Derivative (LYCD) obtained using stress conditions as described in Example 1 of U.S. Pat. No. 2,239,345, which is herein incorporated by reference in its entirety.

EXAMPLE 11

Preparation of *Strelitzia nicolai* Aril Extract in Sub-Micron Emulsion Concentrates A sub-micron emulsion concentrate is prepared that contains a *Strelitzia nicolai* aril extract as described in Example 1.

| Ingredient | % |
|---|---|
| Phase (A) | |
| Water | Q.S to 100 |
| Glycerin | 5.00 |
| Phase (B) | |
| TrimethylolpropaneTricaprylate/Tricaprate | 18.0 |
| Cetearyl alcohol | 2.0 |
| Ceteareth 20 | 2.0 |
| Glyceryl stearate | 2.0 |
| BHT | 0.01 |
| Phase (C) | |
| Example 1 Extract | 1.0 |
| Phenoxyethanol, Caprylyl Glycol and Chlorphenesin | 0.75 |

Procedure:
1. Combine Phase A and heat to 75° C. Mix until uniform.
2. Combine Phase B and heat to 75° C. Mix until uniform.
3. Add Phase A to Phase B while slow mixing Phase B. Mix for 20 minutes and turn off the heat.
4. In a side kettle, pre-mix Phase C and add to the batch when it reaches a temperature below 40° C. Mix until cool to room temperature.
5. Pass through into Niro (High Pressure Homogenizer) for 2 or 3 time. Check the particle size and pH.

While the invention has been described above with references to specific embodiments thereof, it is apparent that many changes, modifications and variations can be made without departing from the invention concept disclosed herein. Accordingly, it is intended to embrace all such changes, modifications, and variations that fall within the spirit and broad scope of the appended claims.

What is claimed is:

1. A method for accelerating the degradation of bilirubin accumulated in the skin of a human suffering from a skin condition, comprising contacting the skin with a topical composition comprising:
   (a) an extract from a bilirubin-producing plant;
   (b) a preservative; and
   (c) a dermatologically-acceptable vehicle;
   wherein (a) is present in an amount from about 0.5% to about 20%; (b) is present in an amount from about 0.001% to about 3.0%; and (c) is present in an amount from about 75% to about 99.05%, to thereby alleviate the skin condition by said contacting.

2. The method according to claim 1, wherein the extract contains components which cause accelerated degradation of bilirubin.

3. The method according to claim 1, wherein the extract is derived from the whole bilirubin-producing plant, part of the plant, the seed of the plant, or a cell culture of the plant.

4. The method according to claim 1, wherein the bilirubin-producing plant is from the genus *Strelitzia* or *Phenakospermum*.

5. The method according to claim 1, wherein the bilirubin-producing plant is from the genus *Strelitzia*.

6. The method according to claim 1, wherein the bilirubin-producing plant extract is from the species *Strelitzia nicolai*.

7. The method according to claim 1, wherein the bilirubin-producing plant extract is taken from the seeds of the bilirubin-producing plant species *Strelitzia nicolai*.

8. The method according to claim 1, wherein the bilirubin-producing plant extract is taken from the arils of the seeds of the bilirubin-producing plant *Strelitzia nicolai*.

9. The method according to claim 1, wherein the bilirubin-producing plant extract is present in an amount from about 0.5% to about 5%.

10. The method according to claim 1, wherein the topical composition diminishes dark pigments of the human skin when applied topically.

11. The method according to claim 10, wherein the dark pigments of the human skin is due to accumulation of blood and blood degradation by-products.

12. The method according to claim 10, wherein the dark pigment is a result of the skin condition selected from the group consisting of: (a) bruising; (b) dark circles under the eyes; (c) spider veins; and (d) port wine stains.

13. The method of claim 1, wherein the bilirubin-producing plant extract is included in a delivery system selected from the group consisting of:
(a) liposome;
(b) niasome;
(c) polymerisome; and
(d) dendrimerosome.

14. The method according to claim 1, wherein the condition is bruising.

15. The method according to claim 1, wherein the condition is dark circles under the eyes.

16. The method according to claim 1, wherein the condition is spider veins.

17. The method according to claim 1, wherein the condition is port wine stains.

18. The method according to claim 1, wherein the bilirubin-producing plant extract is present in an amount from about 0.5% to about 1%.

19. The method according to claim 1, wherein the bilirubin-producing plant extract is present in an amount from about 0.5% to about 10%.

20. The method according to claim 1, wherein the bilirubin-producing plant extract is present in an amount from about 0.5% to about 15%.

* * * * *